United States Patent [19]

Khalil et al.

[11] 4,205,063

[45] May 27, 1980

[54] LOW IRRITANT CONDITIONING SHAMPOO COMPOSITION

[75] Inventors: Ezzat N. Khalil, Oak Park; Ali N. Syed, Hazelcrest, both of Ill.

[73] Assignee: Johnson Products Co., Inc., Chicago, Ill.

[21] Appl. No.: 29,382

[22] Filed: Apr. 12, 1979

[51] Int. Cl.² .................................................. A61K 7/06
[52] U.S. Cl. ...................................... 424/70; 424/359
[58] Field of Search .............................................. 424/70

[56] References Cited

U.S. PATENT DOCUMENTS

| | | | |
|---|---|---|---|
| 3,496,110 | 2/1970 | Shumway et al. | 424/70 X |
| 3,928,251 | 12/1975 | Bolich, Jr. et al. | 424/70 X |
| 3,950,417 | 4/1976 | Verdicchio et al. | 424/70 X |
| 3,962,418 | 6/1976 | Birkofer | 424/70 |
| 3,990,991 | 11/1976 | Gerstein | 424/70 X |
| 4,009,256 | 2/1977 | Nowak, Jr. et al. | 424/70 |
| 4,080,310 | 3/1978 | Ng et al. | 424/70 X |

*Primary Examiner*—Dale R. Ore
*Attorney, Agent, or Firm*—Dressler, Goldsmith, Shore, Sutker & Milnamon, Ltd.

[57] ABSTRACT

Shampoo compositions for human hair having low eye irritancy and conditioning properties are prepared. These compositions are comprised of water having dispersed therein a complex consisting essentially of a water-soluble cationic cellulose ether derivative and an amphoteric surfactant. The complex is dispersed by a mixture of nonionic surfactants consisting essentially of a fatty acid N,N-diethanolamide and a polyoxyethylene sorbitan fatty acid ester. The shampoo compositions are prepared by first dissolving the cationic cellulose ether derivative, admixing the amphoteric surfactant which forms the complex, admixing the nonionic surfactants which disperse the complex and then heating the admixture to assist dispersion of the ingredients.

7 Claims, No Drawings

LOW IRRITANT CONDITIONING SHAMPOO COMPOSITION

DESCRIPTION

1. Technical Field

The present invention relates to shampoos for human hair.

2. Background Art

Cream rinses and conditioners have been used for the past several decades to assist detangling and combing of freshly shampooed, wet hair. Attempts have been made to combine the cleaning properties of a shampoo with the detangling and ease of combing derived from the use of a cream rinse or conditioner into one product. Such attempts have usually failed because the agent deposited upon the hair to impart conditioning properties tended to build-up upon repeated shampooings.

A problem found generally with shampoos alone is that they tend to irritate the eye when inadvertently dripped or splashed therein. Sodium chloride (salt) is frequently used as a shampoo viscosity builder to help avoid the problem of shampoo dripping into the user's eyes. However, when salt is used in sufficient quantities to build the shampoo viscosity and thereby lessen the tendency for splashing or dripping, the stability of the system on aging often suffers and salt itself can also be an eye irritant.

U.S. Pat. No. 3,990,991 discloses a detangling and conditioning shampoo. This shampoo is based upon an amphoteric, imidazoline surfactant, a cationic surfactant and a cryptoanionic surfactant. [Cryptoanionic surfactants are described therein as compounds of the formula R—O—$(R_1O)_n$—$(CH_2)_m$—$CO_2H$ where R is a long chain alkyl group, $R_1$ is ethylene or propylene, n has a value of about 3 to 9, and m is at least 1.] The above patent also discloses previous attempts to make detangling shampoos which were based upon a cationic cellulose ether derivative, triethanolamine lauryl sulfate and lauric diethanolamide. Such shampoos are stated as being inefficient detanglers compared to an independently used cream rinse.

Disclosure of the Invention

The present invention relates to detangling hair shampoo compositions having low eye irritancy and a pH of about 6.0 to about 7.0. These compositions are comprised of water having dispersed therein a complex consisting essentially of a water-soluble cationic cellulose ether derivative and an amphoteric surfactant. The two components of the complex are present in the composition at about 0.25 to about 2.5 and about 5 to about 12 weight percents, respectively. This complex is dispersed in the shampoo composition by a mixture of nonionic surfactants consisting essentially of about 1 to about 10 weight percent $C_{12}$–$C_{18}$ fatty acid N,N-diethanolamide and about 0.5 to about 7 weight percent polyoxyethylene sorbitan fatty acid ester, the ester being selected from the group consisting of $C_{12}$–$C_{18}$ fatty acid monoesters and triesters. All of the above weight percentages are based upon the total weight of the shampoo composition.

The water-soluble cationic cellulose ether derivative is a compound having a chain of anhydroglucose units with substituent groups pendant therefrom and spaced along the chain. These compounds also contain a plurality of quaternary nitrogen-containing groups having from zero to 3 moles of quaternary nitrogen-containing groups per anhydroglucose unit. The average molecular weights of these cationic cellulose ether derivatives is about 10,000 to about 4,000,000.

The amphoteric surfactant is a compound of the formula

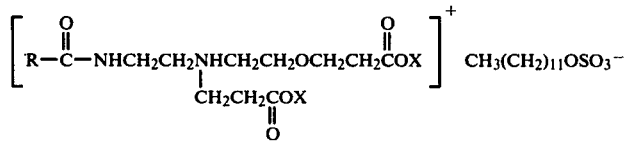

where

is selected from the group consisting of $C_{12}$–$C_{18}$ fatty acids, and X is selected from the group consisting of alkali metal cations.

This invention also discloses a method of producing these shampoo compositions. According to this method, the cationic cellulose ether derivative is first dissolved in deionized water having a temperature no higher than about ambient. The amphoteric surfactant is then added to form the complex along with the nonionic surfactants which disperse the complex as it is being formed. The above admixture is then heated to about 78°–80° C. to assist dispersion of the complex. The dispersing complex is agitated until dispersion is substantially complete, and the dispersion then is cooled with agitation to about ambient temperature.

One advantage of the shampoo compositions of this invention is that little or no build-up is observed when subjects shampoo their hair at a rate of about four times monthly.

Another advantage of the shampoo compositions of the instant invention is that their viscosities are sufficient to minimize dripping once the shampoo is applied to the head, and should the shampoo get into the user's eyes, the shampoo formulations of this invention have a low level of eye irritancy.

Yet another advantage of these shampoo formulations is that they not only clean the hair and give good combing properties, but they also provide sufficient conditioning to the wet hair to allow good detangling and combing when compared to independently used cream rinses.

DESCRIPTION OF THE PREFERRED EMBODIMENTS

The conditioning detangling hair shampoos of the present invention are aqueous compositions having a hair conditioning complex and complex-dispersing agent therein.

The hair conditioning complex contemplated by this invention consists essentially of two components. The first component is a water-soluble, quaternary nitrogen-containing cellulose ether having a backbone chain of anhydroglucose units with pendant substituent groups bearing a full positive charge spaced along the anhydroglucose backbone. The pendant substitutent groups are spaced about the anhydroglucose units along the chain, thereby making the substituent groups themselves pendant and spaced along the chain. These cellulose ether derivatives also contain a plurality of quaternary nitrogen-containing groups with each anhydroglucose unit having from zero to three quaternary nitrogen-containing groups. These materials are prepared having average molecular weights from about 10,000 to about 4,000,000 and their preparation is described in U.S. Pat. No. 3,472,840.

These cationic cellulose ether derivatives are commercially available under the trade name POLYMER JR from the Union Carbide Corporation. The presently available materials include POLYMER JR-125, POLYMER JR-400 and POLYMER JR-30M. Of these three polymers, POLYMER JR-30M, having an average molecular weight of about 600,000 is preferred as it provides better conditioning properties than do the other derivatives.

The water soluble cationic cellulose ether derivative may be present in the composition at about 0.25 to about 2.5 weight percent of the total composition. Preferably it is present at about 1.5 weight percent of the total composition. If less than about 0.25 weight percent of the total composition of the cationic cellulose ether derivative is used, there is little complex formation and little conditioning effect observed. When greater than about 2.5 weight percent of the total is present, the composition becomes difficult to rinse, gives the hair an oily feel and leads to build-up on the hair.

The second essential component of the hair conditioning complex is comprised of an amphoteric surfactant of the formula

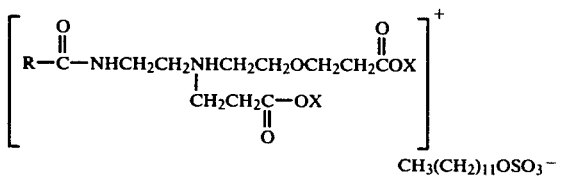

where

is selected from the group consisting of $C_{12}-C_{18}$ fatty acids and X is selected from the group consisting of alkali metal cations. While

may be selected from single fatty acids in the group $C_{12}-C_{18}$ including unsaturated fatty acids, or groups thereof, preferably

includes those fatty acids derived from coconut oil. While X may be an alkali metal cation, such as lithium, sodium or potassium, preferably X is the sodium cation. The preferred amphoteric surfactant is available from the Miranol Chemical Co., Inc. under the name MIRANOL ® 2MCA-ESF.

This complex forming amphoteric surfactant may be present at about 5 to about 12 percent by weight of the composition, but preferably it is present at about 8.5 percent by weight of the total composition. When less than about 5 weight percent is present, foaming and cleaning properties decrease and above about 12 weight percent increased eye irritability is found.

The hair conditioning complex of the instant invention is dispersed by a mixture comprised essentially of two types of nonionic surfactant. The first type is a $C_{12}-C_{18}$ fatty acid N,N-diethanolamide. Preferably, the $C_{12}$ or lauric acid derivative is used because of its solubility characteristics and high foaming properties. The preferred, N,N-diethanolamine lauric acid amide is available from many sources under various trade names. It is designated in the *CTFA Cosmetic Ingredient Dictionary*, 2nd ed., published by The Cosmetic, Toiletry and Fragrance Association, Inc. (hereinafter CTFA dictionary) as lauramide DEA.

The N,N-diethanolamide may be present at about 1 to about 10 weight percent of the total mixture, and preferably at about 5 weight percent of the total composition. When used at less than about 1 percent, the composition becomes unstable with the complex losing its dispersability; additionally, foaming is reduced. When used at greater than about 10 percent, eye irritation can become a problem.

The second component of the conditioning complex-dispersant is another type of nonionic surfactant. This material is a polyoxyethylene sorbitan fatty acid ester, with the esterifying fatty acid being selected from the group consisting of $C_{12}-C_{18}$ fatty acids wherein an average of about 1 or 3 of said acids are esterified per polyoxyethylene sorbitan molecule. The preferred nonionic surfactant is a mixture of laurate esters of sorbitol and sorbitol anhydrides (sorbitan) consisting predominantly of the mono-ester condensed with about 20 moles of ethylene oxide. This surfactant is designated in the CTFA dictionary as Polysorbate 20 and is also known in the art as polyoxyethylene (20) sorbitan monolaurate and is available from several commercial sources.

The polyoxyethylene (20) sorbitan monolaurate may be present in the composition at about 0.5 to about 7 weight percent of the total, and preferably is present at about 3 weight percent of the total composition. When less than about 0.5 percent of this material is used, the resulting shampoo formulation becomes irritating to the eyes of test animals, and when greater than about 7 percent is used, the composition tends to lose its stability.

In addition to the above hair conditioning complex forming and dispersing agents, other materials may be included in the composition to enhance its commercial success. Among these additional materials are buffering agents such as citric acid and boric acid which are used to keep the pH of the composition at about 6.0 to about 7.0, with a pH of about 6.5 being preferred. Preservatives such as boric acid, imidazolidinyl urea, methyl p-hydroxybenzoate and the like may be included. A sequesterant such as disodium ethylenediaminetetraacetate may also be included to chelate metal ions which may be present in tap water used by the consumer or as minor impurities in various of the constituents of the composition. Fragrances and herbal extracts including extracts from rosemary leaves, birch leaves and sap, clover blossoms, sage leaves and the like are included as may be desired, as are cosmetically approved colorants. The shampoos of this invention may also contain emollients or animal oils such as mink oil and proteinacious materials such as dried nonfat milk.

As the shampoo composition of the present invention comprising water, the hair conditioning complex and complex-dispensing agent is slightly hazy, it has been found advisable to add an opacifying or pearlescent agent to the composition to give it an overall opaque or milky appearance. An example of such an opacifying agent is ethylene glycol monostearate which is commercially available from a number of sources. The amount of the opacifying agent used is not critical to this invention and should be sufficient to give the desired opacity without being wasteful. It has been found that use of about 2 percent by weight of ethylene glycol monostearate gives sufficient opacity to the shampoo compositions of this invention without wasteage. It should also be mentioned that ethylene glycol monostearate has some surfactant properties and is nonionic. However, the presence of this nonionic surfactant does not appreciably alter the dispersing effects of the above two essential nonionic surfactants.

To prepare the shampoo compositions of this invention, one begins with deionized water at a temperature no higher than about ambient. To this water is added the water soluble cationic cellulose ether derivative. As usually furnished, the cationic cellulose ether derivative is a solid particulate product and it is preferably added through a fine mesh screen to avoid the addition of any lumps of the polymeric powder which might tend to retard dissolution. Prior to the addition of the cationic cellulose derivative, a propeller-type mixer is set into the deionized water and started at its maximum speed. The solid cationic cellulosic polymer is then dispersed into the agitated water and the resulting solution is mixed until thickening occurs.

After thickening, the amphoteric surfactant is added along with the N,N-diethanolamide and the polyoxyethylene sorbitan fatty acid ester. The amphoteric surfactant, as supplied, is an aqueous solution which is about 34 percent active, while the nonionic surfactants are supplied as liquids which are each about 100 percent active. (Although supplied as a less than completely active solution, the amounts of amphoteric surfactant otherwise mentioned herein are based on the percent active ingredient.) These materials may be mixed prior to admixture into the aqueous cationic cellulosic polymer solution or they may be added individually. Upon addition, the amphoteric surfactant forms a complex with the cationic cellulose ether derivative and this complex is dispersed as it is formed by the combined nonionic surfactants. If premixing of the latter three ingredients is not accomplished prior to their addition to the aqueous solution, it is preferable to add the nonionic surfactants prior to the addition of the amphoteric surfactant lest the hair conditioning complex precipitate from solution or become otherwise difficult to subsequently disperse. If the resultant admixture becomes too viscous, a sweep mixer may be used in addition to the propeller-type mixer.

Upon addition of the above four components to the water, the admixture is heated to about 78° to 80° C. to assist dispersion and when that temperature is reached, heating is stopped while agitation is continued until the resultant hair conditioning complex is substantially dispersed in the composition. The composition is then allowed to cool to about ambient temperature. A shampoo prepared as hereinabove outlined has the desired conditioning, detangling and low eye irritancy properties, a viscosity at about 25° C. of about 5,000 centipoises to about 75,000 centipoises, and has a hazy appearance. The pH may be adjusted to be within the desired range of about 6.0 to about 7.0, and preferably about 6.5.

Additives such as buffering agents, preservatives, sequestrant, protein, protenacious materials and animal oils may be added to the water and mixed prior to the addition of the cationic cellulose ether derivative. If a pearlescent agent is used, it is preferably added along with the surfactants which assist the despersability thereof. It has been found that addition of materials which are sensitive to heat such as herbal extract, fragrance and dyes should be forestalled until the shampoo composition is in its cooling stage and preferably after the composition has reached a temperature of about 50° C. Examples of complete commercial type formulations are given hereinbelow.

EXAMPLES 1-3: Conditioning Detangling Shampoo of Low Eye Irritancy

| Components and Procedural Instructions | (weight percents of total shampoo) EXAMPLES | | |
|---|---|---|---|
| | 1 | 2 | 3 |
| Deionized water in a stainless steel, steam jacketed tank equipped with propeller-type and sweep mixers, and add: | 65.12 | 61.12 | 56.62 |
| Citric acid | 0.45 | 0.45 | 0.45 |
| Boric acid | 0.80 | 0.80 | 0.80 |
| Preservatives | 0.33 | 0.33 | 0.33 |
| Na$_2$EDTA (Note 1) | 0.10 | 0.10 | 0.10 |
| Dried nonfat milk | 0.10 | 0.10 | 0.10 |
| Mink oil | 0.10 | 0.10 | 0.10 |
| Mix for about 15 minutes with propeller-type mixer. Set propeller-type mixer to maximum speed and add: | | | |
| Cationic cellulose ether derivative (Note 2) | 0.50 | 1.50 | 1.00 |
| Pass solid particles through fine mesh screen to avoid addition of lumps. Mix until thickening and add with mixing: | | | |
| Amphoteric surfactant (34 weight percent active material in water.) (Note 3) | 22 | 25 | 30 |
| Lauramide DEA | 5 | 5 | 5 |
| Polyoxyethylene (20) sorbitan monolaurate | 3 | 3 | 3 |
| Ethylene glycol monostearate | 2 | 2 | 2 |
| Continue mixing, and if too viscous, turn on sweep mixer. Heat until the contents are at about 78°-80° C. and then turn off heat. Stir until dispersion is substantially complete. Force cool to about 50° C. and add: | | | |
| Herbal extract (Note 4) | 0.10 | 0.10 | 0.10 |
| Colorant (1% solution) | 0.10 | 0.10 | 0.10 |
| Fragrance | 0.30 | 0.30 | 0.30 |

-continued

Mix until the composition reaches about ambient temperature; and adjust pH to about 6.5.

Note 1. Disodium ethylenediaminetetraacetic acid.
Note 2. A water soluble cationic cellulose ether derivative having a chain of anhydroglucose units with substituent groups pendant therefrom and spaced along the chain, the cellulose ether derivatives containing a plurality of quaternary nitrogen-containing groups having zero to 3 quaternary nitrogen-containing groups per anhydroglucose unit, commercially available under the trade name POLYMER JR-30M from Union Carbide Corporation.
Note 3. An amphoteric surfactant available from the Miranol Chemical Company, Inc. under the trade name designation MIRANOL® 2MCA-ESF having the formula

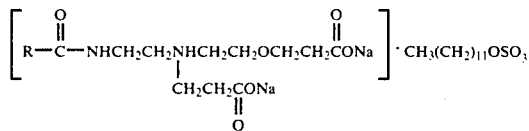

wherein R—C— includes fatty acids derived from coconut oil.
Note 4. The herbal extract includes extracts from rosemary leaves, birch leaves and sap, clover blossoms extract, and sage leaves extract and is commercially available under the trade name designation EXTRAPONE #5 Special from Dragoco, Inc.

SHAMPOO VISCOSITIES

| Example | Viscosity (cps) |
|---------|-----------------|
| 1 | 7,000 ± 1,000 |
| 2 | 45,000 ± 10,000 |
| 3 | 61,000 ± 4,000 |

When the above shampoos are used to wash the hair of human subjects, conditioning and detangling properties similar to those of an independently used cream rinse are obtained along with good cleaning and foaming properties. Little if any buildup is observed when used at a rate of about four shampooings per month.

Studies on test animals indicate that these shampoos have low oral toxicities by standard LD$_{50}$ tests, are not primary skin irritants and are not ocular irritants using Draise test score data.

The invention is defined by the claims which follow.

We claim:

1. A conditioning, detangling hair shampoo composition with low eye irritancy having a pH of about 6.0 to about 7.0 comprising water having dispersed therein a hair conditioning complex consisting essentially of:
    (A) a water-soluble cationic cellulose ether derivative having a chain of anhydroglucose units with substituent groups pendant therefrom and spaced along said chain, said cellulose ether derivative containing a plurality of quaternary nitrogen-containing groups having from zero to 3 moles of quaternary nitrogen-containing groups per anhydroglucose unit, said cellulose ether derivative having an average molecular weight of about 10,000 to about 4,000,000, and
    (B) an amphoteric surfactant of the formula

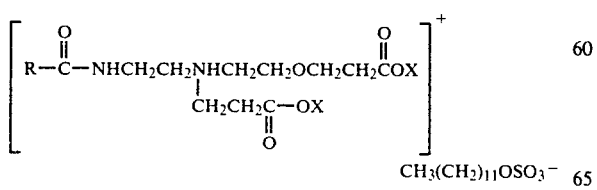

where

is selected from the group consisting of saturated fatty acids containing twelve to eighteen carbon atoms and unsaturated fatty acids containing twelve to eighteen carbon atoms, and X is an alkali metal cation; said cationic cellulose derivative being present in the composition at about 0.25 to about 2.5 weight percent and said amphoteric surfactant being present in the composition at about 5 to about 12 weight percent; said complex being dispersed by a mixture of nonionic surfactants consisting essentially of:
    (C) about 1 to about 10 weight percent fatty acid N,N-diethanolamide wherein the fatty acid contains twelve to eighteen carbon atoms, and
    (D) about 0.5 to about 7 weight percent polyoxyethylene sorbitan fatty acid ester, said ester being selected from the group consisting of a polyoxyethylene sorbitan fatty acid monoester wherein the fatty acid of said monoester contains twelve to eighteen carbon atoms and a polyoxyethylene sorbitan fatty acid triester wherein the fatty acid of said triester contains twelve to eighteen carbon atoms; all of said weight percentages being based upon the total weight of said shampoo composition.

2. The composition according to claim 1 wherein

includes fatty acids derived from coconut oil and X is the sodium cation.

3. The composition according to claim 1 wherein said cationic cellulose ether derivative has an average molecular weight of about 600,000.

4. The composition according to claim 1 wherein said N,N-diethanolamide is N,N-diethanolamine lauric acid amide.

5. The composition according to claim 1 wherein said sorbitan fatty acid ester is comprised of polyoxyethylene (20) sorbitan monolaurate.

6. The composition according to claim 1 wherein said cationic cellulose ether derivative has an average molecular weight of about 600,000 and is present at about 1.5 weight percent; said amphoteric surfactant is present at about 8.5 weight percent,

includes fatty acids derived from coconut oil and X is sodium; said N,N-diethanolamide is present at 5 weight percent and is N,N-diethanolamine lauric acid amide; and said sorbitan fatty acid ester is polyoxyethylene (20) sorbitan monolaureate and is present at about 3 weight percent.

7. A method of producing a low eye irritancy conditioning and detangling hair shampoo composition comprising the steps of
    providing deionized water in a mixing container at no higher than about ambient temperature;
    dissolving about 0.25 to about 2.5 water-soluble cationic cellulose ether derivative having an average molecular weight of about 10,000 to about 600,000 and a chain of anhydroglucose units with substituent groups pendant therefrom and spaced along said chain, said cellulose ether derivative containing a plurality of quaternary nitrogen-containing groups having from zero to 3 moles of nitrogen-containing group per anhydroglucose unit;

admixing into said solution a premixed surfactant composition comprising:

(A) about 5 to about 12 weight percent of an amphoteric surfactant of the formula

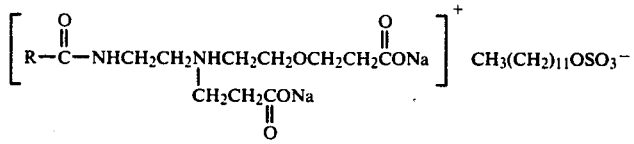

where

is selected from the group consisting of saturated fatty acids containing twelve to eighteen carbon atoms and unsaturated fatty acids containing twelve to eighteen carbon atoms, to form a complex with said cationic cellulose ether derivative, and (B) nonionic surfactants consisting essentially of about 1 to about 10 weight percent fatty acid N,N-diethanolamide wherein the fatty acid contains twelve to eighteen carbon atoms and about 0.5 to about 7 weight percent polyoxyethylene sorbitan fatty acid ester, said ester being selected from the group consisting of a polyoxyethylene sorbitan fatty acid monoester wherein the fatty acid of said monoester contains twelve to eighteen carbon atoms and a polyoxyethylene sorbitan fatty acid triester wherein the fatty acid of said triester contains twelve to eighteen carbon atoms, said nonionic surfactants dispersing said complex as said complex is formed, all of said weight percentages being based upon the total weight of said shampoo composition;

heating said admixture to about 78° to about 80° C. to assist dispersion of said complex;

agitating said heated admixture until said dispersion is substantially complete; and cooling said dispersion with agitation to about ambient temperature.

* * * * *